(12) United States Patent
Ding et al.

(10) Patent No.: US 10,131,595 B2
(45) Date of Patent: Nov. 20, 2018

(54) PROCESS FOR PRODUCTION OF XYLENES THROUGH INTEGRATION OF METHYLATION AND TRANSALKYLATION

(71) Applicant: GTC Technology US LLC, Houston, TX (US)

(72) Inventors: Zhongyi Ding, Katy, TX (US); Weihua Jin, Katy, TX (US); Joseph C. Gentry, Houston, TX (US); Mircea Cretoiu, Sugar Land, TX (US)

(73) Assignee: GTC Technology US LLC, Houston, TX (US)

( * ) Notice: Subject to any disclaimer, the term of this patent is extended or adjusted under 35 U.S.C. 154(b) by 0 days.

(21) Appl. No.: 13/830,112

(22) Filed: Mar. 14, 2013

(65) Prior Publication Data

US 2013/0267746 A1    Oct. 10, 2013

Related U.S. Application Data

(60) Provisional application No. 61/620,830, filed on Apr. 5, 2012.

(51) Int. Cl.
*C07C 6/06* (2006.01)
*C07C 2/86* (2006.01)
*C07C 6/12* (2006.01)

(52) U.S. Cl.
CPC ............... *C07C 6/06* (2013.01); *C07C 2/864* (2013.01); *C07C 6/126* (2013.01); Y02P 20/125 (2015.11)

(58) Field of Classification Search
USPC ......................................... 585/470
See application file for complete search history.

(56) References Cited

U.S. PATENT DOCUMENTS

| 4,053,388 | A | * | 10/1977 | Bailey | C10G 59/02 208/89 |
| 5,321,183 | A |   | 6/1994  | Chang et al. |   |
| 6,459,006 | B1 |   | 10/2002 | Ou et al. |   |
| 7,902,414 | B2 | * | 3/2011  | Ou | B01J 29/06 585/446 |
| 8,940,950 | B2 | * | 1/2015  | Ellrich | C07C 2/864 208/50 |
| 2006/0155155 | A1 |   | 7/2006 | Ghosh et al. |   |
| 2010/0040517 | A1 | * | 2/2010 | Brown | C07C 1/24 422/600 |
| 2011/0178354 | A1 | * | 7/2011 | Negiz | C07C 2/76 585/467 |
| 2013/0190546 | A1 | * | 7/2013 | Xu | C07C 2/76 585/470 |
| 2013/0261364 | A1 | * | 10/2013 | Ercan | B01J 37/04 585/475 |

\* cited by examiner

*Primary Examiner* — In Suk C Bullock
*Assistant Examiner* — Ali Z Fadhel
(74) *Attorney, Agent, or Firm* — Winstead PC

(57) ABSTRACT

The inventive process is directed to the production of xylenes through integration of aromatics methylation and transalkylation. This integrated process maximizes the production of xylenes and eliminates or minimizes the production of benzene.

2 Claims, 3 Drawing Sheets

PROCESS FOR PRODUCTION OF XYLENES THROUGH INTEGRATION OF METHYLATION AND TRANSALKYLATION

CROSS-REFERENCES TO RELATED APPLICATIONS

This Application claims the benefit under 35 U.S.C. § 119(e) of U.S. Provisional Patent Application Ser. No. 61/620,830 filed Apr. 5, 2012, which is incorporated herein by reference in its entirety as if fully set forth herein.

FIELD OF THE INVENTION

The claimed invention relates to a process for producing xylenes through the methylation of aromatic compounds using methanol coupled with transalkylation. This integrated process maximizes the production of xylenes and eliminates or minimizes the production of benzene.

The claimed methods are directed to producing $C_8$ aromatic hydrocarbons comprising fractionating an aromatic hydrocarbon containing feed stream, methylating at least a portion of the aromatic hydrocarbons fractionated from the feed stream to form a methylated aromatic hydrocarbon-enriched fraction, and reacting at least a portion of the methylated aromatic hydrocarbon-enriched fraction in a transalkylation reaction to provide a transalkylation effluent comprising the $C_8$ aromatic hydrocarbons.

BACKGROUND OF THE INVENTION

Paraxylene is a valuable chemical intermediate used in the production of terephthalic acid, which in turn is used in the production of polymers such as polytrimethyleneterephthalate (PTT), polybutyleneterephthalate (PBT) and polyethyleneterephthalate (PET). Given the large market for PET plastics and fibers, in addition to other end products produced from paraxylene, there is a substantial demand for paraxylene in high purity.

Catalytic reforming generally refers to the conversion (or "aromatization") of a naphtha hydrocarbon feed, as a crude oil fraction, to the major products of benzene, toluene, and the xylene isomers. To maximize paraxylene production by utilizing the aromatic compounds from the reforming process, the shortage of available methyl groups must be addressed. The integration of aromatic methylation with transalkylation addresses this issue, and is an effective means to increase methyl groups on aromatic ring and maximize the production of mixed xylenes and paraxylene. Furthermore, by increasing the methylation of the aromatic compounds of the feed stream, the benzene production can be minimized or eliminated.

SUMMARY OF THE INVENTION

An embodiment of the invention is directed to a process for the production of xylenes through the integration of aromatics methylation with methanol and aromatics transalkylation. The shortage of methyl groups is satisfied by using a methyl group from methanol in the aromatics methylation unit prior to the transalkylation step.

The claimed invention is associated with methods for producing $C_8$ aromatic hydrocarbons by the transalkylation of non-$C_8$ aromatic hydrocarbons, for example $C_6$ and $C_7$ aromatic hydrocarbons. Transalkylation refers to the reactions that result in a molecule, introduced into a transalkylation reaction gaining an alkyl group and another molecule, introduced into the transalkylation reaction, losing an alkyl group.

DETAILED DESCRIPTION OF EXEMPLARY EMBODIMENTS

The feed stream, according to aspects of the invention, is any aromatic hydrocarbon containing stream, and preferably comprises $C_9$ or $C_{10}$ aromatic hydrocarbons. Representative feed streams include fractions of reformate (i.e., catalytic reforming effluent).

Figure 1:
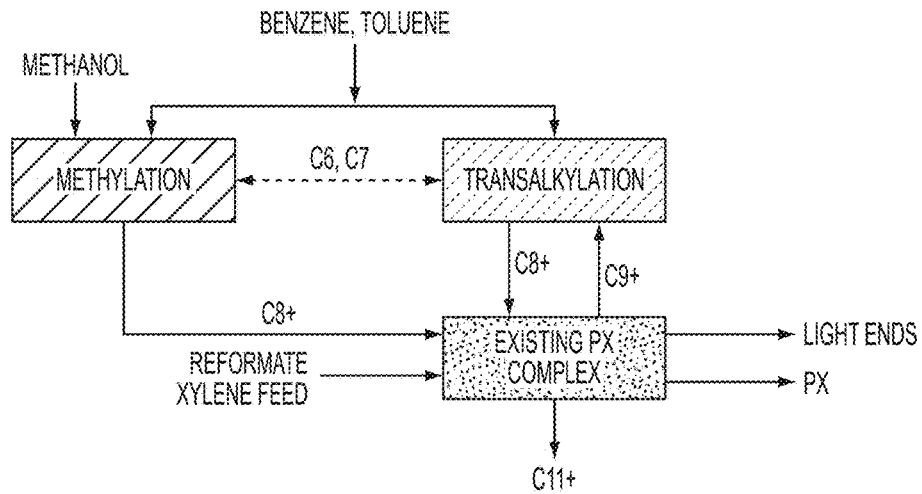
FIG. 1 shows a representative process that may be used in an aromatic complex for producing $C_8$ aromatic hydrocarbons and particularly paraxylene in accordance with an embodiment of the invention.

Representative methods comprise fractionating the feed stream to provide an aromatics fraction. As illustrated in FIG. 1, the aromatics fraction from the feed stream is subjected to a methylation step to generate a methylated aromatic hydrocarbon-enriched fraction. In an embodiment of the invention, the aromatics fraction is methylated using methanol as a methyl-donor. The methylation step provides the basis for increasing the production of paraxylene following the subsequent transalkylation step. A methylated aromatic hydrocarbon-enriched fraction is subjected to a transalkylation step to form paraxylene (PX). In certain embodiments of the invention, the methylated aromatic hydrocarbon-enriched fraction that is used in the transalkylation step is derived from the aromatics fraction arising from the reforming process. In other embodiments of the invention, the methylated aromatic hydrocarbon-enriched fraction that is used in the transalkylation step is derived from the methylation of the aromatics fraction from the feed stream. In certain embodiments of the invention the transalkylation step uses at least a portion of the methylated aromatic hydrocarbon-enriched fraction created in the methylation step. The abbreviations used in FIGS. 2-6 represent the compounds as indicated: B (benzene); T (toluene); EB (ethylbenzene); PX (paraxylene), MX (metaxylene); OX (orthoxylene); iPBz (isopropyl benzene); nPBz (n-propyl benzene); MEB (methylethyl benzene); TMB (trimethyl benzene); X (xylene); C9A (C9 aromatics); C8A (C8 aromatics); TA (transalkylation); TM (transmethylation).

In certain embodiments of the invention, the methylation step is carried out at a temperature of 420-600° C. and pressure of 10-100 psig. In some embodiments, a zeolite catalyst is used that is selected from the group consisting of zeolites X, Y and beta, mordenite, silico-alumino-phosphate, H-ZSM5, ZSM-5, ZSM-11, TS-1, Fe-silicalite, TNU-9 and HIM-5.

Methods according to embodiments of the invention comprise, in addition to providing a methylated aromatic hydrocarbon-enriched fraction, reacting this fraction in a transalkylation reaction zone to provide a transalkylation effluent comprising $C_8$ aromatic hydrocarbons.

In certain embodiments of the invention, the transalkylation step is carried out at a temperature of 300-600° C. and pressure of 100-500 psig. In some embodiments, a zeolite catalyst is used that is selected from the group consisting of zeolites X, Y and beta, mordenite, silico-alumino-phosphate, H-ZSM5, ZSM-5, ZSM-11, TS-1, Fe-silicalite, TNU-9 and HIM-5.

Figure 2:
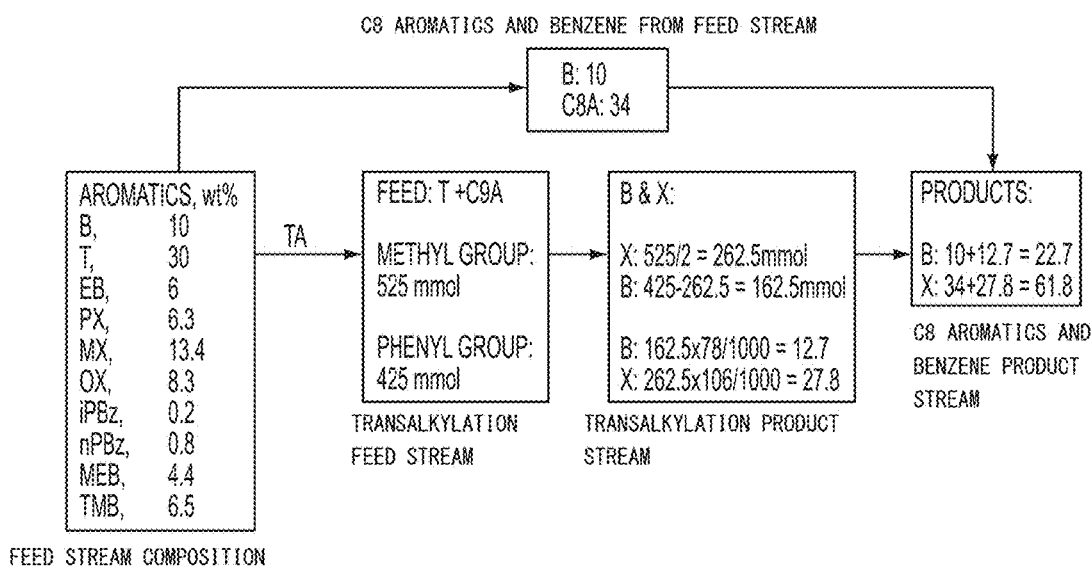
FIG. 2 shows a process for the production of paraxylene in accordance with an embodiment of the invention.

In a typical reformate process, as set forth in FIG. 2, an aromatics fraction is subjected to a transalkylation (TA) step. In an embodiment of the invention, the feed for the transalkylation step is toluene (T) and a $C_9$ plus aromatic ($C_9$A+). In certain embodiments of the invention, the $C_9$ aromatic used in the transalkylation step is trimethyl benzene (TMB). In an embodiment of the invention, the products formed as a result of the transalkylation step in a typical reformate process is a mixture of $C_8$ aromatics (xylene isomers) and benzene present in an approximate ratio of 1:3. The presence of benzene in the mixture can be attributed to the shortage of methyl groups in a typical reformate from reforming process.

Figure 3:
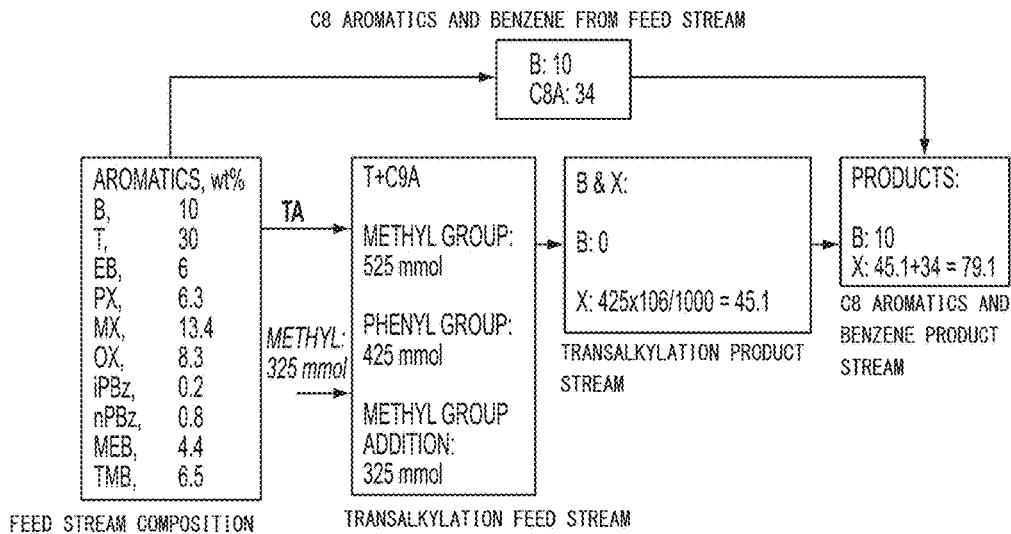
FIG. 3 shows a process for maximizing paraxylene production by the addition of a methyl group in accordance with an embodiment of the invention.

As is shown in FIG. 3, the addition of methyl groups to the transalkylation reaction increases the yield of $C_8$ aromatics relative to benzene in the transalkylation effluent. As is shown in FIG. 3, the ratio of benzene to $C_8$ aromatics (xylene isomers) in the transalkylation effluent is approximately 1:8. In the embodiment shown in FIG. 3, the ratio of methyl groups to phenyl groups present in the transalkylation reaction is around 2:1. It is to be noted that this ratio is higher than the 1.2:1 ratio of methyl groups to phenyl groups that is present in the typical reforming process shown. Therefore, in accordance with embodiments of the invention, it is desirable to have a ratio of methyl groups to phenyl groups in the transalkylation reaction ranging from 1.5:1 to 2.2:1. In certain preferred embodiments of the invention, the ratio of methyl groups to phenyl groups in the transalkylation reaction ranges from 1.95:1 to 2.05:1.

An embodiment of the invention is directed to a process for producing xylenes by using benzene, toluene and $C_9$ plus aromatics. The process comprises the methylation of benzene and toluene to produce mixed xylenes and heavy aromatic compounds, coupled with the transalkylation of existing benzene, toluene, and heavy aromatic compounds, with at least a portion of heavy aromatic compounds in the transalkylation step being from the methylation step.

Figure 4:
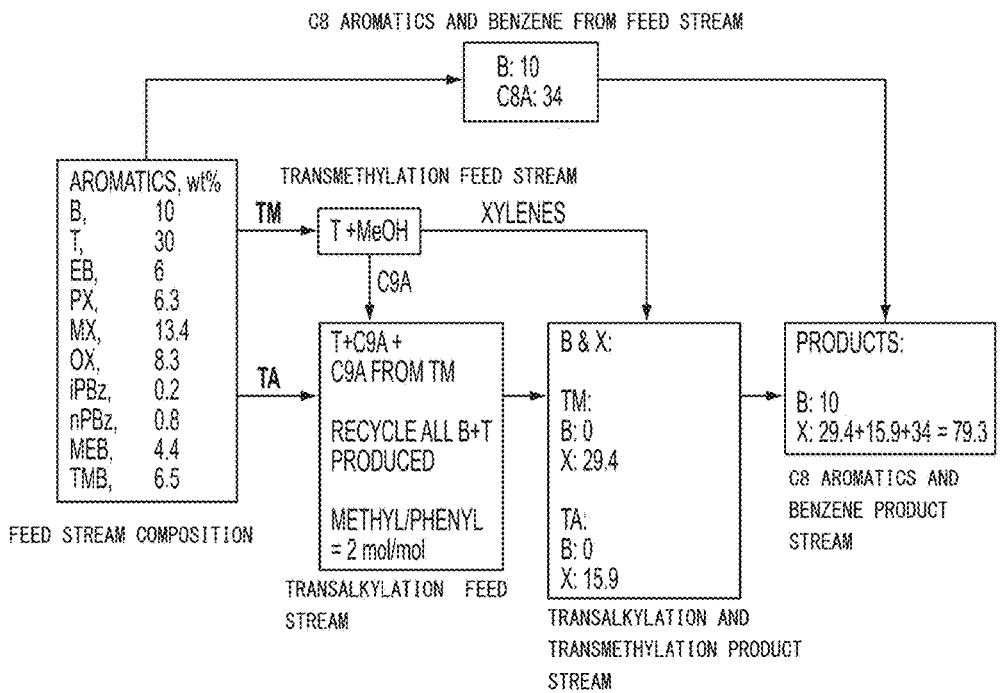
FIG. 4 shows a process for maximizing paraxylene production by the integration of the methylation and transalkylation steps in accordance with an embodiment of the invention.

A representative, non-limiting embodiment of the invention, as it may be practiced in the context of various integrated processes in an overall aromatics complex for producing para-xylene in addition to other products, is illustrated in FIG. 4. In this embodiment, the aromatics fraction in the reactor effluent from the feed stream is subjected to a methylation step to generate a methylated aromatic hydrocarbon-enriched fraction. Specifically, the toluene (T) in the reactor effluent is subjected to methylation. In certain embodiments, the methylation step is carried out using methanol. The methylation process creates a mixture of $C_8$ aromatics such as xylenes and $C_9$ plus aromatics. The $C_9$ plus aromatics are transferred to a transalkylation unit where the transalkylation step is carried out. The ratio of benzene to $C_8$ aromatics (xylene isomers) in the transalkylation effluent is approximately 1:8.

As the preferred molar ratio of methyl group and phenyl group is 2 for the production of xylenes, the transalkylation unit is operated with the molar ratio of methyl group to phenyl group of around 2. In certain embodiments, in the transalkylation unit, the molar ratio of methyl group to phenyl group is in the range of 1.5 to 2.2. In other embodiments, the molar ratio of the methyl group to phenyl group is in the range of 1.95 to 2.05. In certain embodiments of the invention, a portion of benzene and toluene from the reactor effluent is transferred to the methylation step. In other embodiments, all of benzene and toluene from the reactor effluent is transferred to the methylation step.

In certain embodiments of the invention, in the methylation step, benzene and toluene are co-fed to one reactor, or separately fed to different reactors. In certain embodiments of the invention, a portion of benzene and toluene in the reactor effluent is transferred to the methylation step. In other embodiments, all of benzene and toluene in the reactor effluent is transferred to the methylation step. In certain embodiments of the invention, in order to satisfy the molar ratio of methyl group and phenyl group of 1.5 to 2.2 in the transalkylation step, a portion of benzene and/or toluene from the methylation step is transferred to the transalkylation step. In other embodiments of the invention, in order to satisfy the molar ratio of methyl group and phenyl group of 1.95 to 2.05 in the transalkylation step, a portion of benzene and/or toluene from the methylation step is transferred to the transalkylation step.

In an embodiment of the invention, the effluents from the methylation step and transalkylation step share the same separation section. In certain embodiments of the invention, benzene and toluene, either mixed or separated, are transferred to the methylation step and the transalkylation step.

Figure 5:
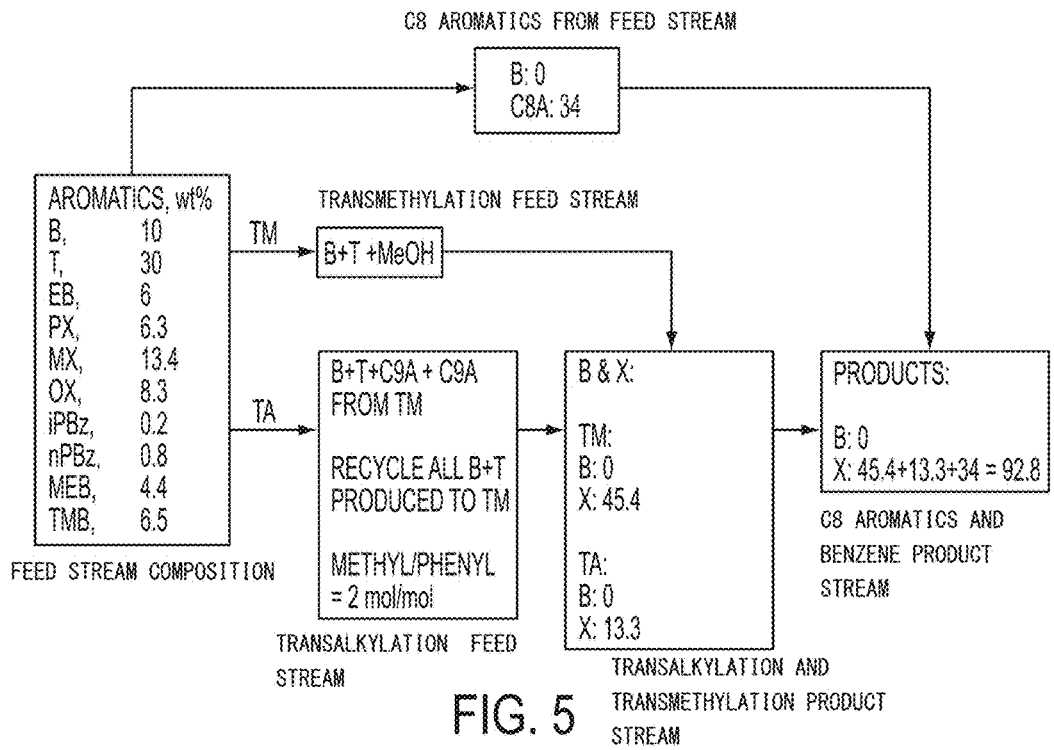
FIG. 5 shows a process for maximizing paraxylene production and eliminating benzene production by the integration of the methylation and transalkylation steps in accordance with an embodiment of the invention.

FIG. 5 shows a process for the production of xylenes in accordance with an embodiment of the invention. As shown in FIG. 5, the benzene and toluene from the reactor effluent are subjected to a methylation step. In certain embodiments of the invention, methylation is carried out using methanol. The methylation step produces a mixture of xylenes. In a transalkylation step, $C_9$ plus aromatics from the reactor effluent or those derived from the methylation step is subjected to transalkylation at a methyl/phenyl ratio of about 2. The products resulting from the transalkyation step are a mixture of xylenes. It is to be noted that little to no benzene is found in the product mixture.

Figure 6:
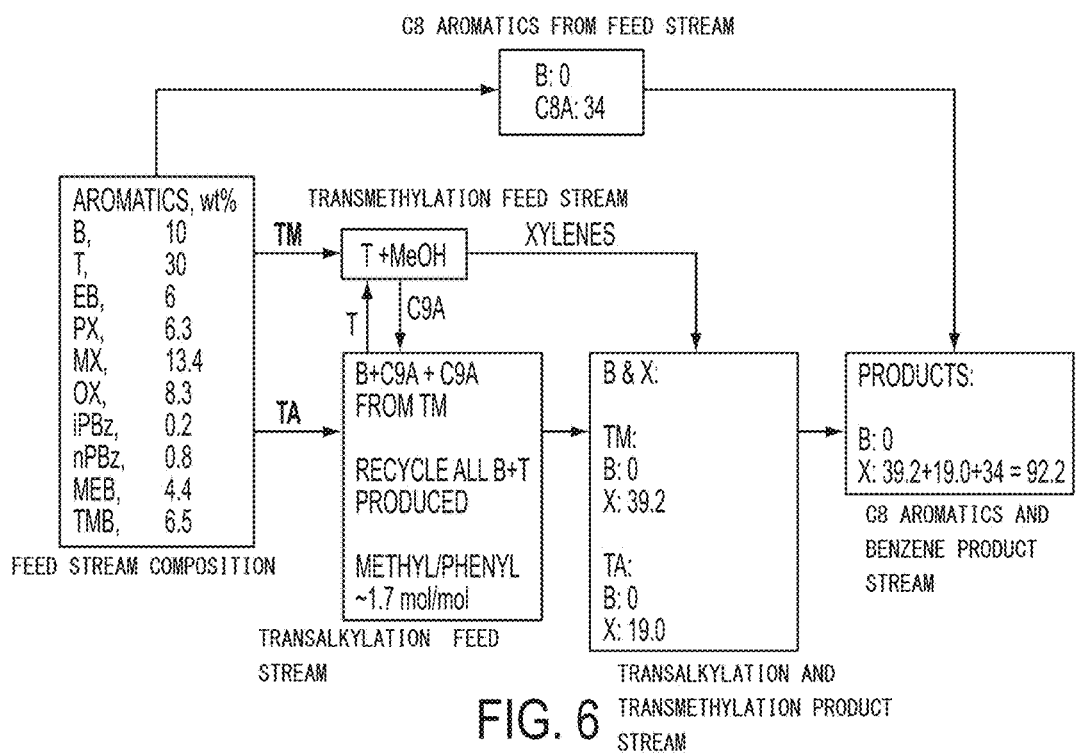
FIG. 6 shows a process for maximizing paraxylene production and eliminating benzene production by the integration of the methylation and transalkylation steps in accordance with an embodiment of the invention.

FIG. 6 shows a process for the production of xylenes in accordance with an embodiment of the invention. As shown in FIG. 5, toluene from the reactor effluent is subjected to a methylation step. In certain embodiments of the invention, methylation is carried out using methanol. The methylation step produces a mixture of xylenes. In a transalkylation step, $C_9$ plus aromatics from the reactor effluent or those derived from the methylation step is subjected to transalkylation at a methyl/phenyl ratio of about 1.7. The products resulting from the transalkyation step are a mixture of xylenes. It is to be noted that little to no benzene is found in the product mixture.

Overall aspects of the invention relate to methods for producing $C_8$ aromatic hydrocarbons, comprising reacting a methylated aromatic hydrocarbon in a transalkylation reaction to provide a transalkylation effluent comprising the $C_8$ aromatic hydrocarbons. Advantageously, the methylated aromatic hydrocarbon is present in a methylated aromatic hydrocarbon-enriched fraction to the transalkylation reaction zone. Those having skill in the art, with the knowledge gained from the present disclosure, will recognize that various changes could be made in these $C_8$ aromatic hydrocarbon production methods without departing from the scope of the present invention. Mechanisms used to explain theoretical or observed phenomena or results, shall be interpreted as illustrative only and not limiting in any way the scope of the appended claims.

What is claimed is:

1. A process for producing $C_8$ aromatics comprising:
   providing a feed stream comprising benzene, toluene, $C_8$ aromatics and at least one of $C_9$ aromatics and $C_{10}$ aromatics;
   separating from the feed stream $C_8$ aromatics, a methylation feed comprising toluene and being free of benzene, and a transalkylation feed comprising benzene and the at least one of $C_9$ aromatics and $C_{10}$ aromatics;
   feeding the methylation feed to a methylation reaction to produce a mixture of benzene, toluene, $C_8$ aromatics and $C_9$+ aromatics;
   feeding the transalkylation feed and the $C_9$+ aromatics produced from the methylation reaction to a transalkylation reaction to convert the at least one of $C_9$ aromatics and $C_{10}$ aromatics and the $C_9$+ aromatics from the methylation reaction to $C_8$ aromatics; and
   transferring a portion of the benzene and toluene produced from the methylation reaction to the transalkylation reaction to maintain a methyl group to phenyl group molar ratio of 1.5 to 2.2 in the transalkylation reaction.

2. The process according to claim 1 in which effluents from the methylation reaction and the transalkylation reaction share a single separation section.

\* \* \* \* \*